(12) United States Patent
Hannapel et al.

(10) Patent No.: US 9,987,103 B1
(45) Date of Patent: Jun. 5, 2018

(54) ORTHODONTIC PROTECTION DEVICE

(71) Applicant: ORVANCE, LLC, Calendonia, MI (US)

(72) Inventors: Eric D. Hannapel, Middleville, MI (US); David Gerard Jablonski, Alto, MI (US)

(73) Assignee: OrVance, LLC, Caledonia, MI (US)

( * ) Notice: Subject to any disclaimer, the term of this patent is extended or adjusted under 35 U.S.C. 154(b) by 228 days.

(21) Appl. No.: 14/610,243

(22) Filed: Jan. 30, 2015

Related U.S. Application Data

(60) Provisional application No. 61/933,542, filed on Jan. 30, 2014.

(51) Int. Cl.
*A61C 7/12* (2006.01)

(52) U.S. Cl.
CPC .................................. *A61C 7/125* (2013.01)

(58) Field of Classification Search
CPC .............. A63B 71/085; A63B 2208/12; A63B 2071/088; A63B 2071/086; A63B 2209/02; A61F 5/566; A61F 5/56; A61F 5/50; A61F 5/58; A61C 7/08; A61C 5/14; A61B 13/00; A61B 1/24
See application file for complete search history.

(56) References Cited

U.S. PATENT DOCUMENTS

| | | |
|---|---|---|
| 3,455,872 A | 7/1969 | Beck |
| 4,497,926 A | 2/1985 | Toy |
| 4,957,783 A * | 9/1990 | Gabryszewski ...... B05B 7/1272 118/300 |
| 5,624,745 A | 4/1997 | Lapidus |
| 6,638,881 B2 | 10/2003 | Lapidus |
| 7,195,484 B1 | 3/2007 | Wagner |
| 7,312,256 B2 | 12/2007 | Borja |
| 7,789,662 B2 | 9/2010 | Van Eikeren et al. |
| 8,007,277 B2 * | 8/2011 | Fischer ................ A61C 19/063 128/859 |
| 2003/0205234 A1 * | 11/2003 | Bardach ............... A61C 19/063 128/861 |
| 2005/0089820 A1 * | 4/2005 | Allred ..................... A61C 5/00 433/215 |
| 2005/0181324 A1 | 8/2005 | Hare |
| 2005/0239015 A1 | 10/2005 | Dragan |
| 2006/0063128 A1 | 3/2006 | Dragan |
| 2007/0185237 A1 | 8/2007 | Rajaiah et al. |
| 2008/0293015 A1 | 11/2008 | Wong et al. |
| 2012/0107768 A1 | 5/2012 | Diedwardo |
| 2012/0199138 A1 * | 8/2012 | Hannapel .............. A61C 7/125 128/859 |

(Continued)

FOREIGN PATENT DOCUMENTS

| | | |
|---|---|---|
| CA | 2858830 A1 | 6/2013 |
| EP | 2544651 A1 | 1/2013 |
| WO | 2011112193 A1 | 9/2011 |

*Primary Examiner* — Ophelia A Hawthorne
(74) *Attorney, Agent, or Firm* — Nyemaster Goode, P.C.

(57) ABSTRACT

An orthodontic protection device including: a protective layer shaped sized to fit over the facial surface of at least one tooth of a human and any orthodontic appliances affixed to the facial surfaces of the at least one tooth, wherein the protective layer includes a moldable material; and an adhesive layer including at least one hygroscopic polymeric material on a facial surface of the protective layer.

20 Claims, 16 Drawing Sheets

(56) References Cited

U.S. PATENT DOCUMENTS

2014/0017637 A1    1/2014   Cinader, Jr. et al.
2015/0037266 A1    2/2015   Boyd et al.
2015/0209120 A1    7/2015   Hannapel et al.

* cited by examiner

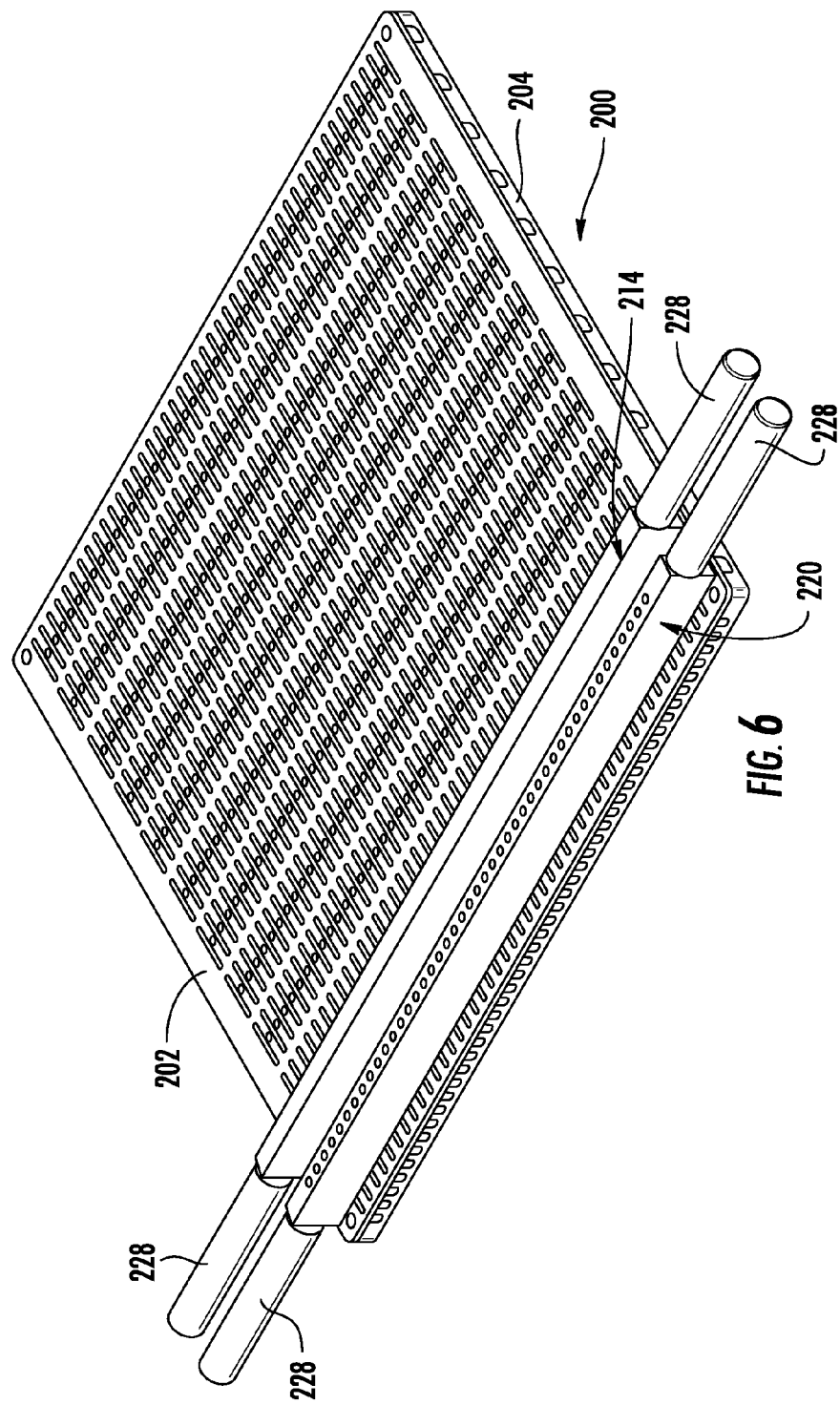

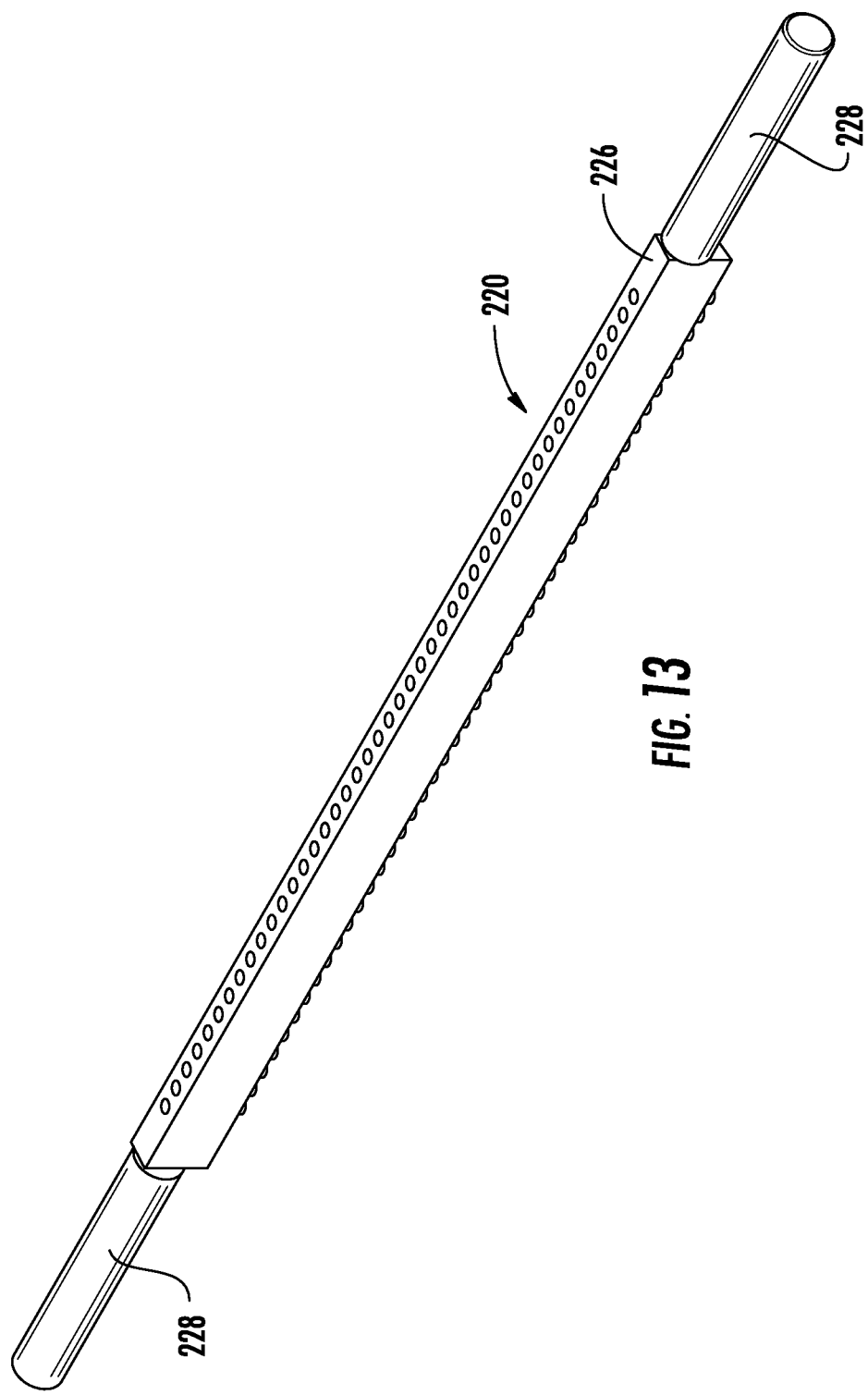

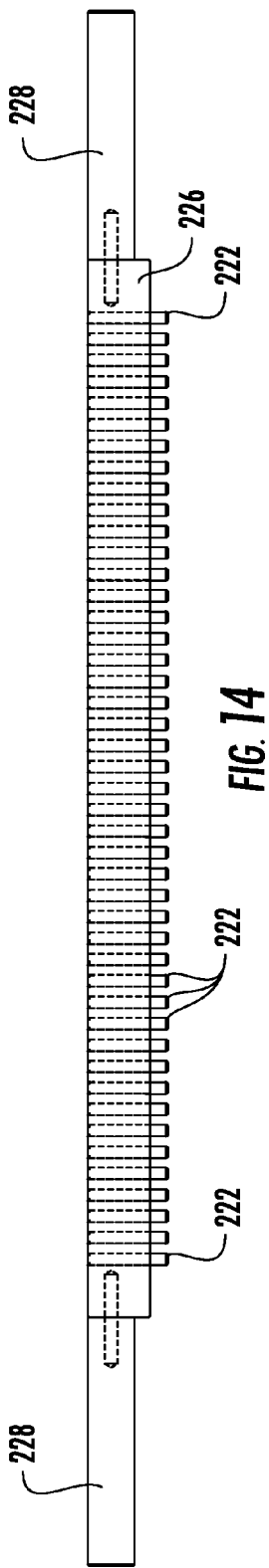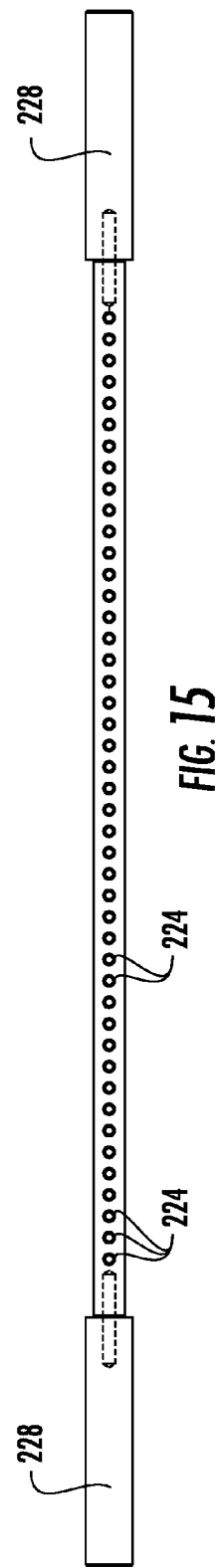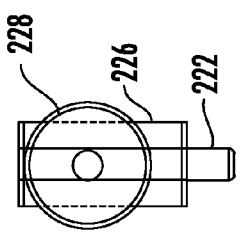

ORTHODONTIC PROTECTION DEVICE

CROSS-REFERENCE TO RELATED APPLICATION

This application claims priority from U.S. Provisional Patent Application Ser. No. 61/933,542 filed Jan. 30, 2014, entitled "Orthodontic Protection Device" the entire specification of which is hereby incorporated by reference.

BACKGROUND

Quite a few devices have been described that offer protections to the soft tissues of the mouth from abrasion by orthodontic braces, but all possess significant drawbacks that have prevented their wide use. One device describes a silicone bracket cap with holes and slits that fit over a bracket and is secured by the main wire, requiring the placement of many caps and a bumpy, irregular feel. Another teaches a silicone shield that employs a room temperature setting silicone that is placed in the mouth and allowed to set. It is then removed from the mouth and trimmed. This is an inconvenient procedure, and sanitary storage must be employed for re-use of the device.

A flat thermoplastic strip has been described that requires heating to between 160-212 degrees Fahrenheit to soften it, whereupon it is pressed and molded onto the teeth and braces. A moldable lip guard has been described that must first be heated in hot water. Another disclosure teaches a two-part curable silicone composition that, upon mixing the parts, yields a putty-like consistency that can be molded over the braces before the cure is complete. The mixing and timing aspects of this device also render it inconvenient to use.

A putty-like, finger-moldable material sold as ORTHOSIL™ Silicone Dental Wax, a product currently on the market, comes in small strips that can be pressed onto the braces to offer protection. ORTHOSIL™ is marketed as a silicon "wax". This material is not an elastomer, but is rather a thixotropic semisolid that is well known to those practiced in the art of silicones. However, even when molded onto and into the brackets and wires of orthodontic braces, it adheres poorly if the braces are moist with saliva. Unfortunately, braces are typically very moist with saliva since the presence of braces in the mouth commonly stimulates excess saliva production. The saliva acts as a lubricant such that even though molded into and onto the brackets and wires of the braces, the material easily dislodges from the braces. As a result, the instructions for the ORTHOSIL™ Dental Wax product state "Your brackets must be completely dry for Silicone wax to adhere properly." This is a very difficult state to achieve in the moist environment of a user's mouth without professional assistance, which is not available for day to day usage.

In addition, this material tends to stick more aggressively to the fingers than to the braces if the braces are wet and the fingers are dry, which is typically the case. This causes the silicone wax material to pull off the braces during attempted application. The following Table 1 shows the lateral force exerted by a Mitutoyo Model 546-133 Dial Tension Gauge required to dislodge a pressed-on 0.080 g piece of ORTHOSIL™ from a variety of surfaces (porcelain being used to model the enamel surface of a tooth).

TABLE 1

| Surface | Force (milli Newtons) |
| --- | --- |
| Dry finger tip | 86 mN |
| Dry porcelain surface | 87 mN |
| Water-wet porcelain surface | <10 mN |

The force required to dislodge the ORTHOSIL™ from a wet "tooth" is a small fraction of the force required to dislodge it from a dry fingertip, indicating almost no adhesion to the wet "tooth" relative to a dry fingertip.

In addition, it is well known to orthodontists that demineralization (decalcification) of tooth enamel often occurs at the edges of brackets cemented to the teeth due to the presence of plaque, resulting in chalky spots on the tooth surface. Studies have shown that demineralization can occur around orthodontic appliances as early as one month into treatment.

SUMMARY

An aspect of the present disclosure is generally directed to an orthodontic protection device that includes: a protective layer shaped and sized to fit over the facial surface of at least one tooth of a human and any orthodontic appliances affixed to the facial surfaces of the at least one tooth, wherein the protective layer comprises a moldable material; and an adhesive layer including at least one hygroscopic polymeric material on a facial surface of the protective layer.

In another aspect of the present disclosure, an orthodontic protection device for one tooth of a user includes: a finger moldable base material, shaped and sized to fit over the facial surface of the one tooth of a human and any orthodontic appliances affixed to the facial surface of the one tooth, wherein the protective layer comprises a moldable material that comprises a thixotropic semi-solid material or a mixture of thixotropic semi-solid materials; and a plurality of beads that form an adhesive layer on a facial surface of the base layer wherein the beads comprise at least one hygroscopic polymeric material and a plasticizer.

Yet another aspect of the present disclosure is generally directed to a method of fabricating and packaging as well as a method for installing the devices of the present disclosure into engagement with a surface on a user's tooth or teeth. In one aspect the method includes the steps of: forming a moldable material into a shape to temporarily cover an orthodontic implement in a user's mouth; and coating a surface of the moldable material with an adhesive layer by applying the adhesive layer to at least one surface of the moldable material, wherein the adhesive layer comprises a hygroscopic polymer. The methods may further include the step of dehydrating the adhesive layer after it is applied to the at least one surface of the moldable material. The step of forming the moldable material may include extruding the moldable material into a moldable rod. The moldable material may be a polymeric material having a glass transition temperature below about 37° C. The step of dehydrating may include heating the adhesive coated moldable material at a temperature of from about 60° C. to about 120° C. and the adhesive layer may be a plurality of discontinuous beads of adhesive. The moldable material may be a silicone polymer compounded (mixed, combined) or in a mixture with either one or both of silica or trimethylsilylated silica. The methods may further include the following steps: using a dimpling tool to create at least one cavity in a facial surface of the moldable rod prior to application of the adhesive layer; cutting the moldable rod into a plurality of orthodontic protection devices; placing at least one orthodontic protection device into a container; and placing a moisture barrier seal on the container to at least substantially prevent moisture migration from between an ambient environment surrounding the container and an interior of the container. The container allows the device to be hygienically used by patients/users, especially when the packaging allows for the devices to be individually packaged in, for example, a blister pack or other hygienic packaging. This allows for in orthodontic office or at home hygienic application of one device at a time. The device may be packaged such that a plurality of devices, each for an individual tooth, is within separate hygienic chambers sealed until time of use.

During application, a method of the present disclosure may include the following steps: opening the container to allow access to the at least one orthodontic protection devices within the container; placing the facial surface of the at least one orthodontic protection devices over a brace on a tooth using a fingertip pressure applied by fingers of a human wherein the adhesive layer operates to retain the at least one orthodontic protection device in position over the brace and into engagement with the brace or the brace and the at least one tooth; and thereafter, using fingertip force to remove the at least one orthodontic protection device from engagement with the brace.

These and other aspects, objects, and features of the present invention will be understood and appreciated by those skilled in the art upon studying the following specification, claims, and appended drawings.

BRIEF DESCRIPTION OF THE DRAWINGS

Various features will become apparent to those skilled in the art from the following detailed description of the disclosed non-limiting disclosure. The drawings that accompany the detailed description can be briefly described as follows:

FIG. 6 is a perspective view of a forming tray assembly with dimpling and spacing tools positioned within the guide cover according to an aspect of the present disclosure.

FIG. 13 is a perspective view of the dimpling tool according to an aspect of the present disclosure.

FIG. 14 is a side elevational view of a dimpling tool according to an aspect of the present disclosure.

FIG. 15 is an elevated bottom view of a dimpling tool according to an aspect of the present disclosure.

FIG. 16 is a side elevational view of a dimpling tool according to an aspect of the present disclosure.

DETAILED DESCRIPTION

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In this specification and the appended claims, the singular forms "a," "an" and "the" include plural reference unless the context clearly dictates otherwise.

An orthodontic appliance shield or guard is disclosed in the form of a flexible guard or shield which is easily installed over an orthodontic appliance. The orthodontic appliance shield or guard protects the surrounding inner soft lip and cheek tissue from contact with the sharp surfaces of the orthodontic appliance if the user's face is accidently struck, with force, such as during an athletic event or when playing a musical instrument. This minimizes the occurrence of cuts and bleeding in the lips and cheeks, which require the athlete to be removed from the athletic contest until the bleeding stops. The orthodontic appliance shield is easy to install and provides a one time, inexpensive, disposable use; while, at the same time, protecting the soft tissue in a user's mouth surrounding the orthodontic appliance from injury during physical contact in, for example, an athletic event, during playing of musical instruments, during when braces are first installed or later after installation.

Figure 1A:
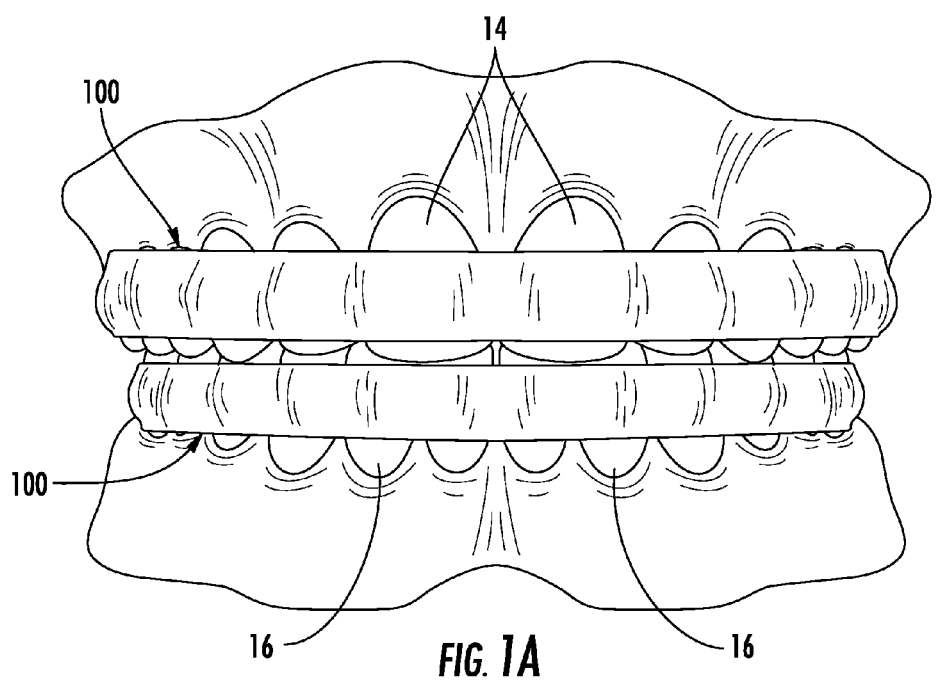
FIG. 1A is a pictorial representation showing the installation of orthodontic appliance guards on both upper and lower sets of teeth.
Figure 1B:
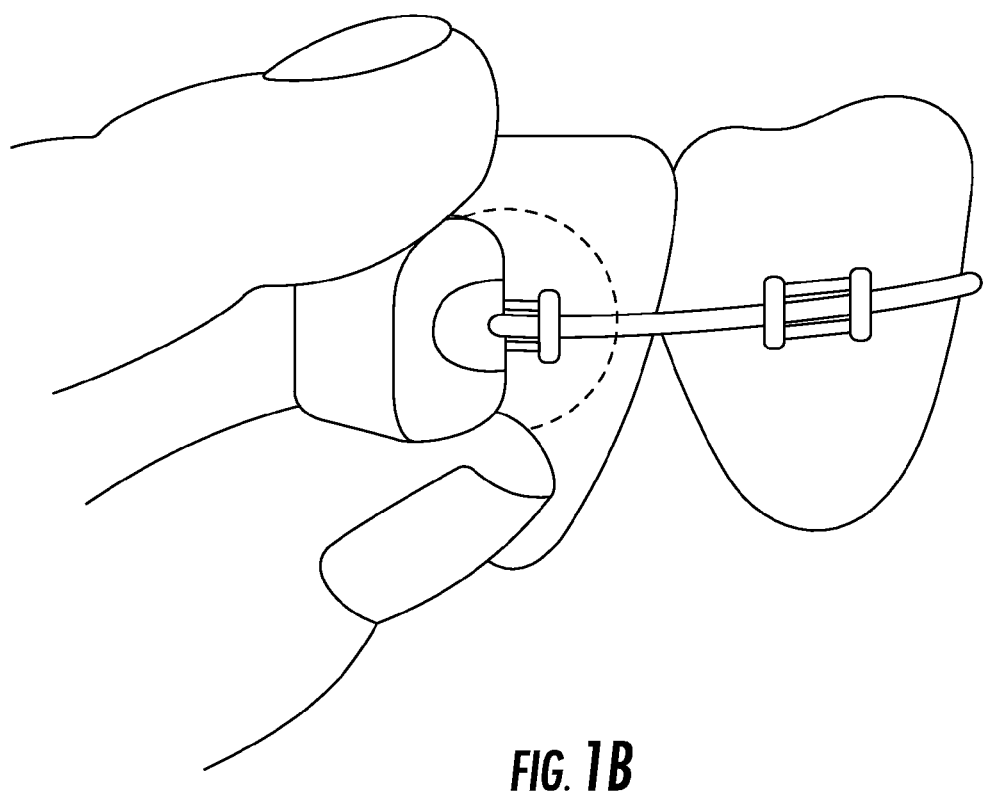
FIG. 1B is a pictorial representation of fingertip application of an orthodontic device onto a single orthodontic bracket.

Referring to FIG. 1, FIG. 1 shows an example of orthodontic protection device applied to either or both of a user's upper teeth 14 and lower teeth 16, respectively. It will be understood that the shape, attachment, length and number of teeth to which the orthodontic protection device 100 is applied is shown in FIG. 1 only by way of example as it will be understood that the orthodontic protection device 100 may take any necessary shape and configuration to suit a particular user's orthodontic requirements.

Figure 3A:
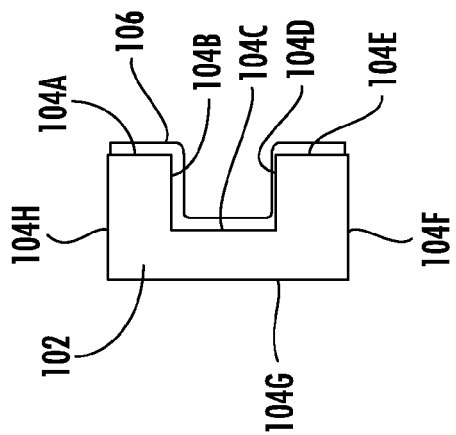
FIG. 3A is an end view of the device shown in FIG. 2.
Figure 2:
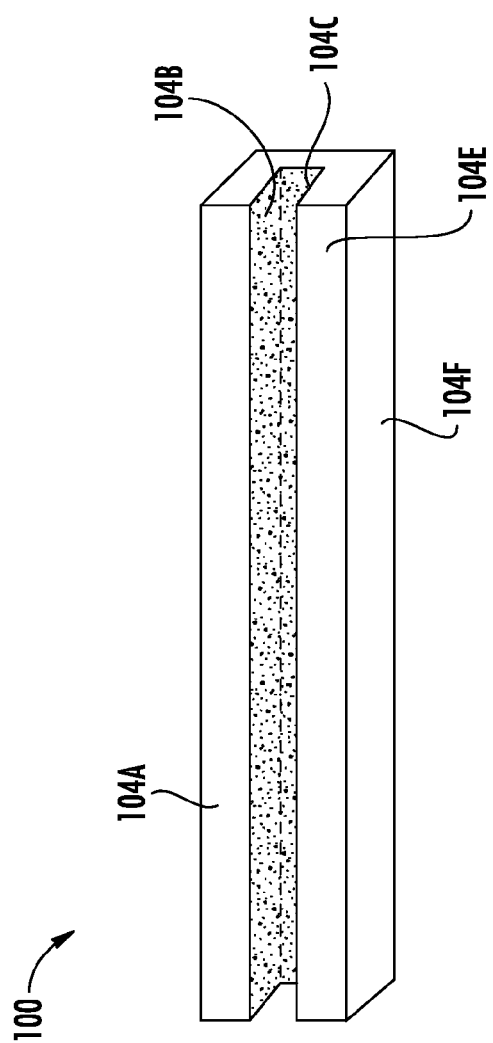
FIG. 2 is a perspective view of another aspect of an orthodontic protection device according to the present disclosure.
Figure 3B:
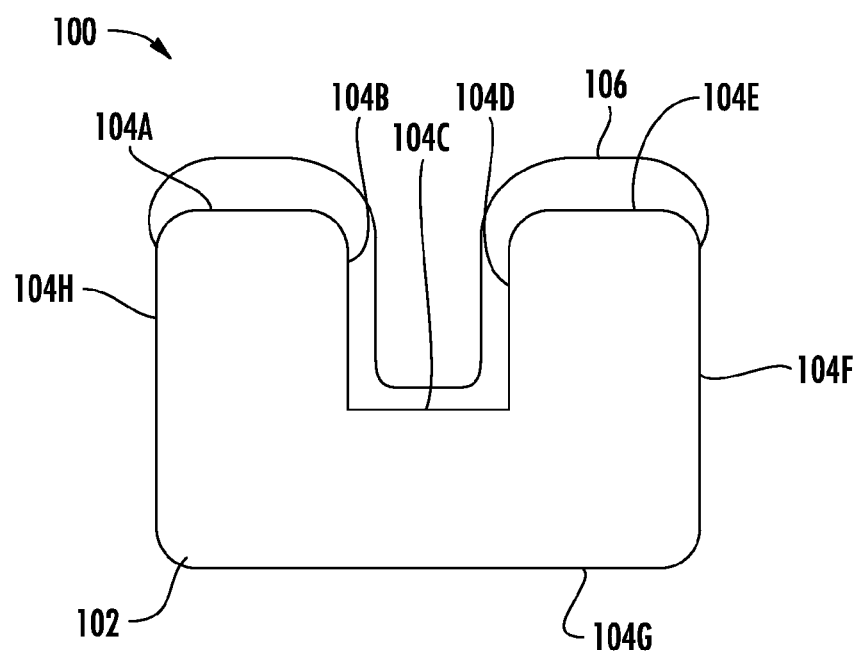
FIG. 3B is an enlarged view of the device of FIG. 3A.
Figure 4A:
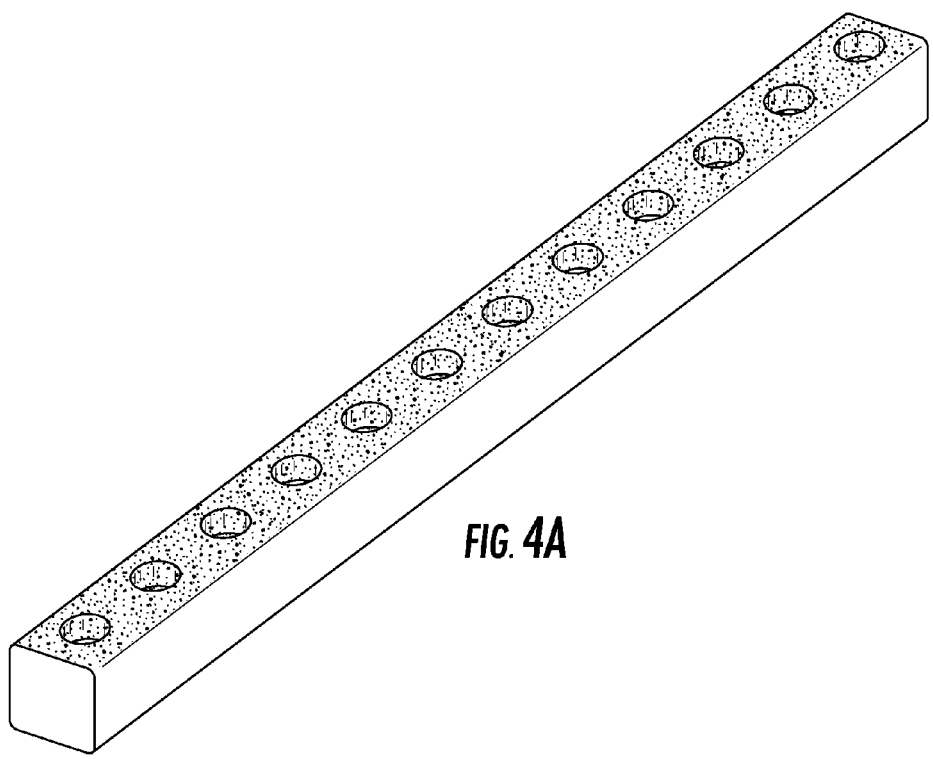
FIG. 4A is a perspective view of a variant of a device having a circular dimpling across its length instead of an elongated configuration and showing the beaded adhesive on the dimpled surface of the device.

The orthodontic protection device 100, shown in FIGS. 1-4A, is formed of an elongated strip of pliable, flexible material. The device is typically sized in width to cover the entire exterior surface of the orthodontic appliances. Although the orthodontic protection device 100 is shown in FIG. 1 as being applied over both of the orthodontic appliances (braces) affixed to the upper teeth 14 and the lower teeth 16 of a user, a single orthodontic protection device 100 can be provided for the upper teeth 14 or for the lower teeth 16 of the user. Additionally, by way of example, as shown in FIGS. 4A and 4B (mono concave cuboidal shape), various lengths of the device and various shapes are contemplated such as, circular or other dish-like configurations having a varying perimeter structure (such as circular, oval, elliptical, polygonal, concave disc shaped, cuboidal, or arbitrary).

The present disclosure is generally directed toward devices for temporarily coating intra-oral, orthodontic implements (e.g., orthodontic brackets and/or arch wires) to reduce discomfort and prevent injury to the soft tissues within a user's mouth. The present disclosure is further directed toward methods of fabricating such devices and methods of applying such devices on the surface of a tooth or the teeth of a wearer of orthodontics.

FIGS. 2 and 3 show a side cross-sectional view and a perspective view of one variation of a device 100 which can be adhered to the facial surfaces of a user's teeth, and/or to any orthodontic implements attached to the user's teeth, to minimize discomfort to the user or minimize damage to the user's soft tissues resulting from an orthodontic implement. Device 100 includes a protective layer 102 composed substantially of a moldable material. The moldable material can in certain variations be formed into a shape suitable to accommodate an orthodontic implement disposed in a user's mouth. For example, with the embodiments of FIGS. 4A and 4B, the protective layer 102 includes an outer rim region (i.e., annular wall) 122 and a cavity region 124 defined thereby.

As used herein, "moldable material" is substantially plastically deformable at a temperature equal to or less than about 37° C. and under a stress reasonably applied by manual pressure. The moldable material is capable of being formed by hand/fingertips and fingertip pressures without the use of tools into a user desired shape. As such, the moldable material can possess one or more of the following properties: viscoelastic properties, viscoplastic properties, thermoplastic properties, thixotropic properties, semi-solid properties, or any other molecular properties which confer the desired moldability. The desired moldability characteristics being: (1) easily moldable into any shape using finger-pressure, and (2) retention of that shape upon cessation of finger-pressure or any other external pressure.

In some variations, the moldable material can comprise a polymeric material. As used herein, a polymeric material can include any material whose molecular structure has at least ten covalently attached monomeric subunits. Plastic properties of a suitable polymeric can be modified, for example, by cross-linking. In some particular instances, the moldable material can comprise a silicone polymer. Suitable examples of moldable material can include, but are not limited to: thermoplastic elastomers (plasticized and non-plasticized) having glass transition temperatures below body temperature (approximately 37° C.); viscoelastic silicone rubber; polydimethylsiloxane combined with fumed silica or trimethylsilylated silica filler; and a mixture of one or more of polydimethylsiloxane, vinyl-functionalized polydimethylsiloxane, silanol-functionalized polydimethylsiloxane, Si—H functional silicone, combined with fumed silica or trimethylsilylated silica filler. The latter material is well known to those practiced in the art of silicone chemistry and is referred to as a silicone High Consistency Rubber (HCR) base. The moldable material is most typically a thixotropic semi-solid material or a mixture of thixotropic semi-solid materials that are finger pressure moldable and that once molded into a shape, retain that shape until additional pressure is applied. Among other examples, the moldable material may comprise, but is not limited to Dow Corning Silastic Q7-4535, Q7-4550, Q7-4565 Biomedical Grade ETR Elastomer, Wacker Elastosil R Plus 4000/50 Silicone Rubber Base; Wacker Elastosil R 401/50 S Silicone Rubber Base, and NuSil MED-4174 Silicone Elastomer. In yet some other variations, the moldable material can comprise one or more food safe color pigments.

Figure 4B:
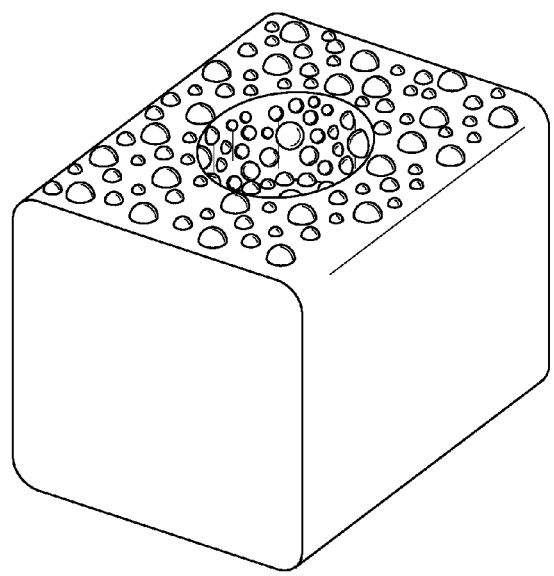
FIG. 4B is a perspective view of a variant of a device having a cuboid configuration instead of an elongated configuration and showing the beaded adhesive on the dimpled surface of the device, which is typically positioned over a single bracket on a single tooth.

Device 100 can include eight (8) surfaces 104A, 104B, 104C, 104D, 104E, 104F, 104G, and 104H. Surfaces 104A, 104B, 104C, 104D, and 104E together form what may be termed a dental contacting surface. Device 100 further includes an adhesive layer 106, which coats at least a portion of device 100 surfaces. In the device of FIGS. 4A and 4B, a similar cross-sectional configuration is envisioned, with surfaces 104C, 104D being the same annular surface and the surfaces 104F and 104H being the same outer annular surface. Such a device may have a diameter of, for example 6 mm (while not being limited thereto), so as to fit over a generally localized area.

The device 100 in FIG. 2 shows surfaces 104A, 104B, 104C, 104E, and 104F visible. The perspective view of FIG. 2 illustrates that the shape of device 100 includes an orthodontic accommodation element, which is a unitary component. The embodiment shown in FIG. 2 is an elongated member with a base and opposing walls that define a longitudinal channel. The interior walls of the extended channel consist of surfaces 104B, 104C, and 104D. When device 100 is employed in a user's mouth, surfaces 104A and 104E may tend to contact the facial surfaces of the user's teeth, while surfaces 104B, 104C, and 104D may tend to contact the surfaces of an orthodontic implement such as orthodontic brackets and/or arch wires. It is important to note that the shape of device 100, shown in FIGS. 2-4, is exemplary only and that in various alternatives, device 100 need not include discrete surfaces 104A, 104B, 104C, 104D, 104E, 104F, 104G, and 104H. The device need only have a shape configured to contact the teeth and orthodontic appliance. In the embodiments of FIGS. 4A and 4B, an annular wall surrounds and defines a cavity.

The moldable material can be partially or completely coated on at least one surface with an adhesive layer 106, which is typically a series of adhesive beads that form the adhesive layer. When the adhesive layer employs beads or other visually perceptible configurations, this function acts as an indicator to tell the user which surface to apply to the tooth or teeth. The dimples or channels may also provide this visual and/or tactile indication to the user prior to application of a device according to the present disclosure The adhesive layer is typically a hydratable, hygroscopic polymeric material to enable adhesion of the device to a user's teeth and or orthodontic implement(s). The solvent is typically water, but another solvent such as alcohol typically ethanol, could be employed. The hydratable hygroscopic polymeric material is typically dehydrated to form a moisture/saliva absorbing adhesive prior to use. The moisture (solvent) loss during dehydration may be anywhere from about 1% to about 100% of moistures, but is more typically a loss of from about 72% to about 82% mass loss as discussed in greater detail in the Examples. Typically, moisture is lost until the adhesive layer is non-tacky.

As used herein, the term "hygroscopic" can be used to describe a material capable of attracting and holding water molecules from the surrounding environment. Suitable hydratable hygroscopic polymeric materials can include, but are not limited to, any material from a list comprising polyvinylpyrrolidones, polyoxazolines, starches, polyacrylic acids, polyacrylates, poly(ethylene glycol), polyvinyl alcohols, carbomers, cellulose derivatives, polysaccharides, pectin, guar gum, natural gums, hydrophilic cellulose ethers, carboxymethyl cellulose, hydroxypropyl cellulose, hydroxypropyl methylcellulose, polyvinyl acetates, polysaccharide gums, xanthan gum, modified food starches, gelatin, animal or fish-based gelatin, cross-linked carboxyvinyl copolymers, cross-linked polyvinylpyrrolidones, polyethylene oxide, alginate, casein, pullulan, and combinations thereof.

The adhesive layer 106 can, on contact with saliva-moistened teeth and or an orthodontic implement, offer initial adhesion of the device to the teeth and/or orthodontic implement and rapidly absorb said saliva. The adhesive layer 106 typically further comprises a plasticizer, which is used to soften the layer or coating of hydratable hydroscopic polymeric material(s). As used herein, the term "plasticizer" can refer to any substance which, when mixed with a hygroscopic polymeric material(s), results in a mixed material of greater plasticity than that of the hygroscopic polymeric material alone. Suitable plasticizers will in many instances be hydrophilic and can include but are not limited to polyols, such as glycerin, sorbitol, xylitol, propylene glycol, and polyethylene glycol having an average molecular weight of from about 200 to about 6000, and esters of polyols such as glycerin triacetate. In yet some other variations, adhesive layer 106 can further comprise tooth enamel strengtheners and remineralizers such as but not limited to sodium fluoride, sodium monofluorophosphate, stannous fluoride, calcium phosphate, sodium silicate, sodium phosphates, trisodium phosphate, and calcium lactate. In yet some other variations, adhesive layer 106 can further comprise a food safe flavor ingredients and/or food safe food colors. Such colors may provide yet another indicator to the user of which surface to apply to the tooth, i.e. the adhesive containing surface.

In a use position, the orthodontic device 100 can be of a length to cover some or all of the exterior surfaces of the orthodontic appliances on the upper and/or lower teeth, and prevents the engagement of the sharp edges and portions of the orthodontic appliances covered by the device 100 with the inner surfaces of the soft tissue of the user's lips or cheeks. This prevents the orthodontic appliance from causing injury to and bleeding from the lip or cheek tissue when an external force, as frequently occurs during a contact or even a non-contact athletic event, brings the soft tissue into forced engagement with the sharp edges, corners, or other portions of the orthodontic appliances.

The orthodontic devices of the present disclosure thus minimize injury to the soft tissue. The devices of the present disclosure can prevent bleeding during an athletic event that previously would have required the athlete to remove himself or herself from the event until the bleeding stopped. The orthodontic devices are useful for mediating and may at least substantially, if not completely, prevent irritation or abrasion resulting from the braces contacting soft tissue.

During use of device 100, a user can initially apply device 100 to the facial surfaces of the user's tooth or teeth and/or to one or more orthodontic implements attached thereto. In some examples, an orthodontic implement can be "braces", comprising brackets and an arch wire. In such examples, initial application would typically be performed such that surfaces 104A and 104E contact the facial surfaces of the teeth. In some such examples, brackets and an arch wire would approximately fit into a longitudinal channel of device 100.

Subsequent to initial application of the device, the user can mold device 100 to tooth/teeth and braces by pinching or otherwise exerting finger pressure applied approximately at surfaces 104F, 104G, and 104H toward the tooth/teeth and/or braces at various locations along the length of device 100. During initial application, water absorption by adhesive layer 106 can produce an initial adhesion. The initial adhesion can prevent device 100 from being pulled off during initial application and/or molding as might otherwise occur due to stickiness between device 100 and user's fingers. A 0.08 g piece of ORTHOSIL™ with adhesive layer 106, when pressed onto a wet porcelain surface, requires >140 mN of force to dislodge it when measured with the aforementioned Mitutoyo Model 546-133 Dial Tension Gauge, indicating a stronger adhesion to wet teeth than to a dry fingertip (see Table 1). Additionally, moisture absorption by adhesive layer 106 can rapidly dry the braces and teeth. The typical finger pressure applied to the finger pressure moldable material is applied by the finger without the use of tools and is from about 20 N to about 90 N, more typically from about 35 N to about 45 N. Finger pressure can vary by gender. Most typically, the applier of the device(s) of the present disclosure will apply finger pressure for about 5 seconds, which in most every instance will cause the device to adhere and contact both the orthodontic device, typically a brace, and the portion of the tooth around the brace. The extent of contact with the tooth will depend on the size of the brace, the tooth, and the amount of finger pressure being applied to the device.

Also, the device shown in FIGS. 2-4 can be modified in a variety of ways to make changes to its shape. For example, any of the surfaces 104A-104E can be curved instead of flat. The length of the device (7 mm), the depth and width of the groove (3 mm), and the widths of surfaces 104A-104E (2 mm) can also be variable, with one or more of these lengths and widths being adjusted to zero (all dimensions are examples only). As shown by comparison of FIGS. 3 and 4, any or all of the corners between surfaces 104A-104E may be square or rounded.

A method 200 of fabricating an orthodontic protection device is shown schematically in FIG. 5. In step 122, a protective layer 102 formed of a moldable material and suitably shaped to temporarily cover an orthodontic implement in a user's mouth is provided. In many instances a suitable shape will be one which is substantially longer in one dimension than in any other, such as a relatively long, narrow cylinder or rectangular prism. In some instances, a suitable shape will be of the type shown above in FIGS. 1-3 with a longitudinal channel operable to accommodate the protrusions of an orthodontic implement. In other instances, the devices of the present disclosure may be of the type shown in FIGS. 4A and 4B with dimples (wells) to accommodate a bracket or brackets. In some instances the devices may have a flat surface lacking a channel, groove, or dimple with the flat surface of the moldable material engaging the orthodontic braces or orthodontic braces and the front surface of the tooth. Suitable moldable materials employed in step 122 can be of the type described above.

In step 124, at least one surface of protective layer 102 is coated with an adhesive layer 106 comprising a hygroscopic polymeric material. Suitable examples of hygroscopic polymeric material are as described above. In some instances, step 126 can be performed by applying an aqueous solution of hygroscopic polymeric material to protective layer 102 and allowing said aqueous solution to dry. In many instances, hygroscopic polymeric material will be applied to one or more surfaces of protective layer 102 which are configured to contact the facial surfaces of a user's teeth and or orthodontic implement, such as surfaces 104A, 104B, 104C, 104D, and/or 104E as described above. In addition, a hydrophilic plasticizer, as described above, can optionally be mixed with the hygroscopic polymeric material prior to application to protective layer 102.

In optional step 126, the applied hygroscopic polymeric material, which comprises an adhesive layer 106 can be dehydrated after application in order to maximize its water absorbing ability. Such dehydration can be achieved, for example, by exposing device 100 to evaporative heat or by air drying at ambient conditions, or by some combination of both.

Figure 5A:
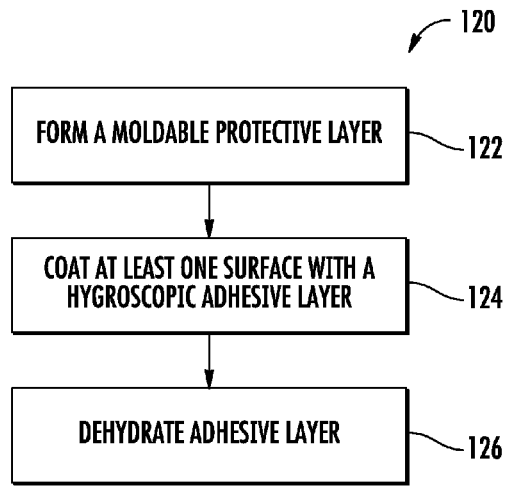
FIG. 5A is a flow chart of a method for fabricating an orthodontic protection device.
Figure 5B:
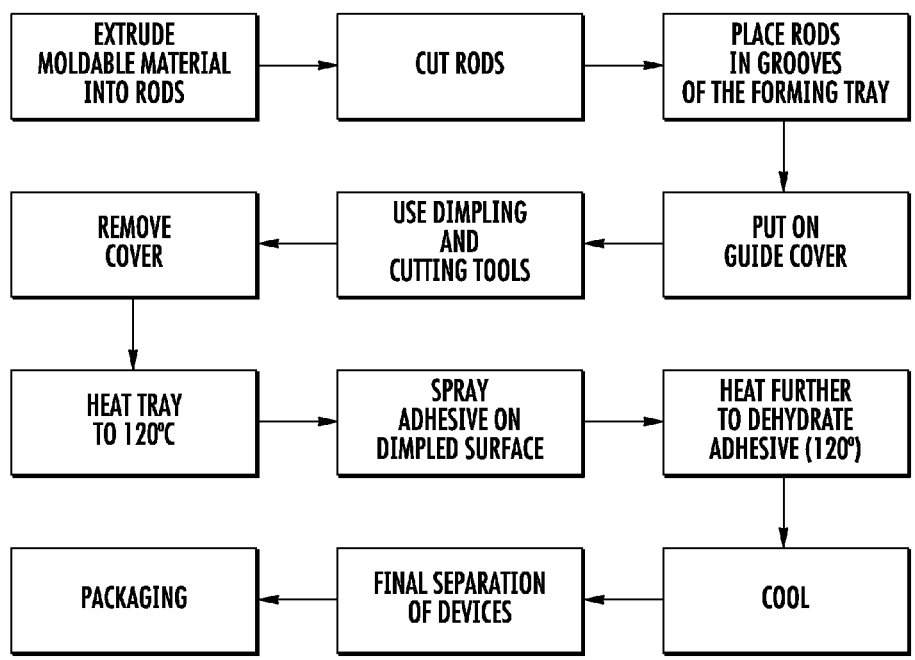
FIG. 5B is a flowchart of another method of fabricating an orthodontic protection device according to the present disclosure.
Figure 7:
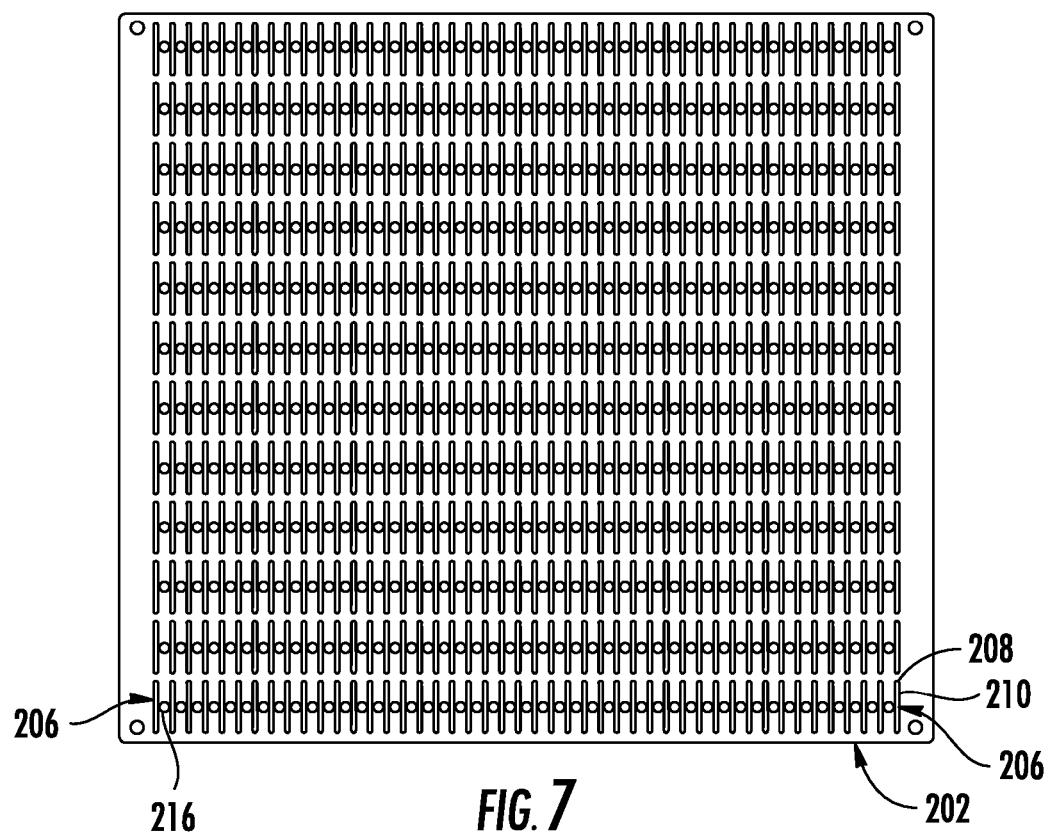
FIG. 7 is a front elevational view of a guide cover according to an aspect of the present disclosure.
Figure 8:
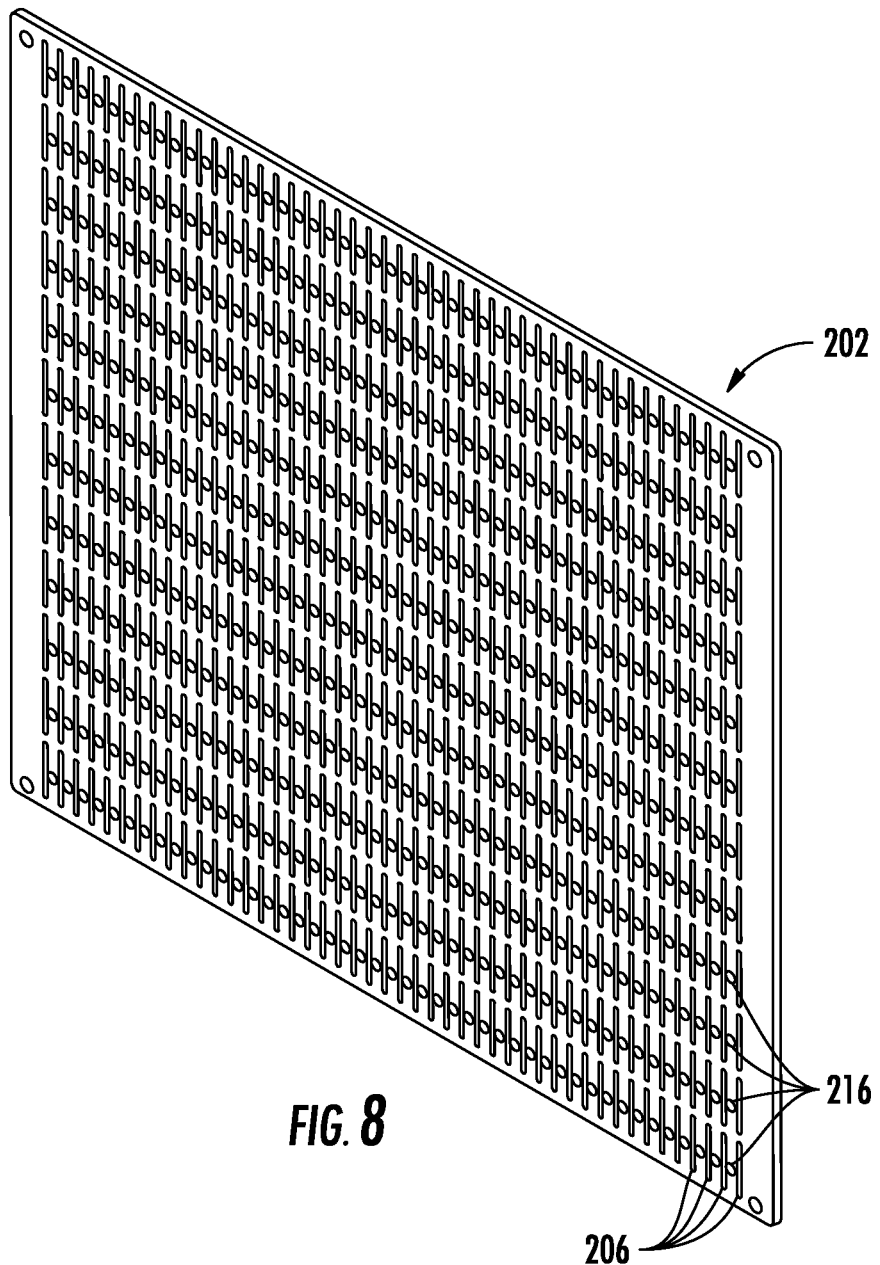
FIG. 8 is a perspective view of a guide cover according to an aspect of the present disclosure.
Figure 9:
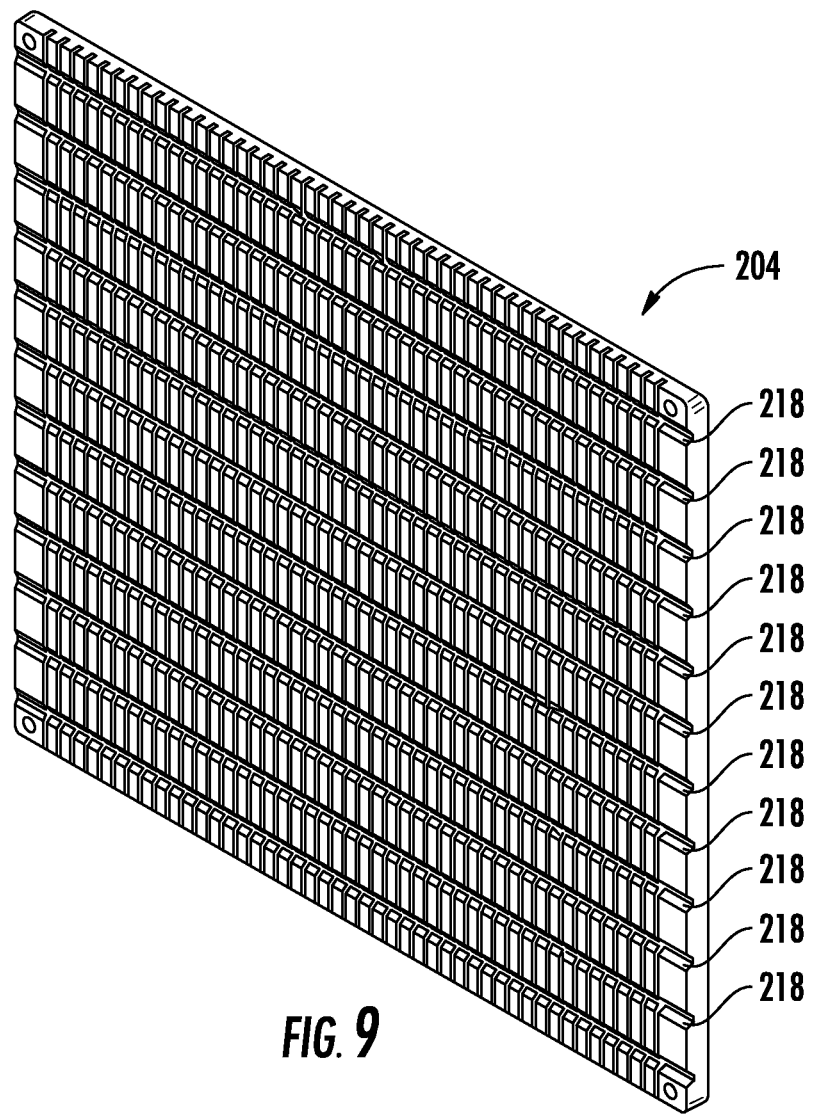
FIG. 9 is a perspective view of a forming tray according to an aspect of the present disclosure.
Figure 10:
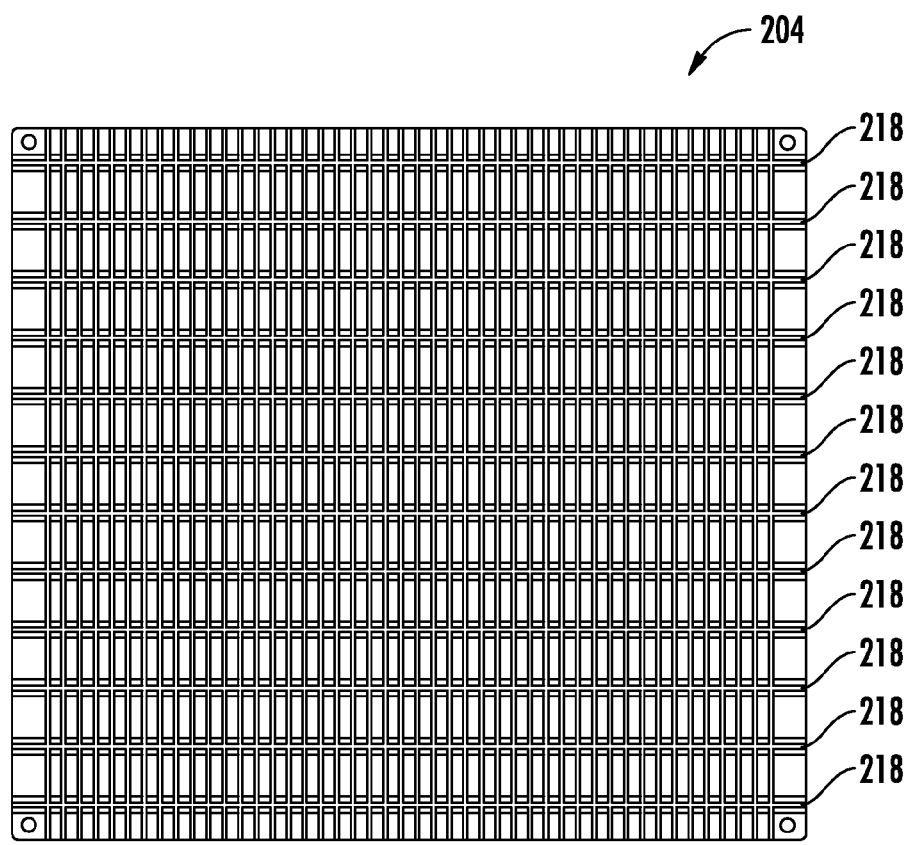
FIG. 10 is a front elevational view of a forming tray according to an aspect of the present disclosure.

An example of one method of fabrication of the orthodontic protection device is shown in FIG. 5A. Another example of a method of fabricating an orthodontic device as depicted in FIG. 4A or 4B is outlined in FIG. 5B. As will be discussed in greater detail later, forming a tray assembly may be used along with other implements and tools including a spacing tool and a dimpling tool. These implements are depicted in FIGS. 6-20. According to the process as shown generally in FIG. 5B, initially, the moldable material, Dow Corning Q7-4550, is extruded using a piston extruder, single screw or twin screw extruder at ambient conditions to yield 3 mm square cross section rectangular rods. The rods are then cut and are laid into the grooves of the forming tray depicted in FIG. 9. The tool guide tray cover depicted in FIG. 7 is then placed onto the top surface of the forming tray to yield the assembly shown in FIG. 6.

Next, the dimpling tool depicted in FIGS. 13-16 is inserted through the guide holes (circular apertures) in the tray cover and the extruded rods of moldable material are dimpled by application of downward force on the rods. Next, the spacing tool 214 depicted in FIGS. 17-20 is inserted through the guide slits (elongated apertures) in the tray cover and the extruded rods of moldable material are cut into individual orthodontic protection devices depicted in FIG. 4b. The tray cover is then removed and the orthodontic devices may or may not be heated in an oven to between 60° C. to 200° C., more typically from about 80° C. to about 160° C., and most typically from about 100° C. to about 140° C. or about 120° C. Thereafter, an aqueous adhesive formulation is applied with an atomizing sprayer, which applies the adhesive and, along with the nature of the silicone material which is hydrophobic, together forms the adhesive beads of the adhesive coating on the facial contacting surface of the devices. Next, the trays are placed back into a 60-200° C. oven for additional sufficient drying of the adhesive coating. Upon removal from the oven, the orthodontic protection devices are individually removed from the tray and placed into suitable packaging. This method may be adapted for producing elongated orthodontic protection devices via extrusion of rods with a groove in them fashioned by an appropriately shaped die head opening using the same trays and tools described above with the exception of the dimpling tool, which would not be used. Other methods of fabricating these orthodontic protection devices include, but are not limited to, extrusion of the moldable material at low temperatures to increase its green strength, allowing for rapid and automated dimpling and cutting with or without the use of the trays and tools depicted in FIGS. 6-20.

In another method, the present devices may be produced by modifying the above process in the following manner. Adhesive is applied after the moldable material has been dimpled. Thereafter, the tray containing the product is transferred to the oven and heated to drive off moisture from the adhesive. Next, the spacing tool is applied to the product to yield a string of devices that are engaged to one another via a thin layer of moldable material. The string may be manually or machine removed from the tray and thereafter transferred to a typically non-stick surface (pure TEFLON®, ceramic non-stick material or TEFLON® coated material). In the next step the devices are finish cut into the individual devices, typically done so manually or by using an automated cutting machine. The individual, separate devices are then manually or by machine placed into packaging having a moisture barrier such that the adhesive coating does not substantially rehydrate.

As shown in FIGS. 6-20, the forming tray assembly 200 typically includes a tool guide tray cover 202 and a forming tray 204. The tool guide tray cover 202 can be secured in place over the top of the forming tray 204 or may be simply placed over and held in place by gravity. It is possible the cover 202 could be in a snap fit arrangement or a clamped arrangement over the forming tray 204. The tool guide tray cover 202, as discussed above, contains a series of elongated apertures 206, which typically have rounded ends 208 and elongated center portions 210. Generally speaking, the elongated apertures are parallel with one another or at least substantially parallel with one another and sized to receive spacing tool prongs 212 of the spacing tool 214. Generally speaking, the spacing tool and elongated apertures mate with one another and allow for some back and forth movement of the spacing tool, if desired, within the elongated apertures to space apart the individual devices of the present disclosure as discussed above.

Circular or substantially circular apertures 216 are also typically spaced apart on the cover 202 and generally align with the grooves 218 in the tray 204 that receive the extruded moldable material of the present disclosure. The dimpling tool 220 (See FIGS. 13-16) has a plurality of spaced apart pins 222 that can be set to any user determined length, typically a user predetermined length. The spaced apart pins 222 are typically frictionally fit, but may be otherwise engaged, into channels 224 that extend though the pin support bar 226. Both the dimpling tool and the spacing tool typically have tools handles, one engaged to each end of the tool to allow a user to manually engage the tools with the assembly 200. Once engaged, the handles 228 facilitate easy insertion of the tools into the apertures of the cover and also facilitate movement of the tool into engagement with the moldable material and within the assembly, especially in the case of the spacing tool, which is permitted to move back and forth within the elongated apertures. The spacing tool prongs align and are spaced to mate with the elongated apertures, if desired. Similarly, the spaced apart pins are spaced to mate with the circular apertures. The spaced apart pins would not necessarily need to be cylindrical, as shown, and could be any shape to match the desired shape of the recess to be made in a surface of the device 100. In the case of the embodiment shown, the pin is cylindrical to form a substantially cylindrical detent/recess in the top surface of the device 100, but the shape is not critical. The shape of the pin generally matches (while still allowing for vertical movement) the apertures of the cover.

Figure 11:
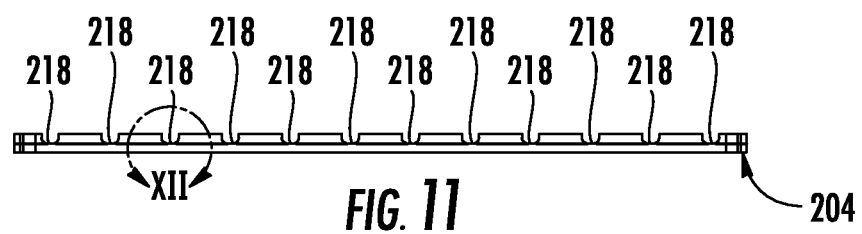
FIG. 11 is a side elevational view of a forming tray according to an aspect of the present disclosure.
Figure 12:
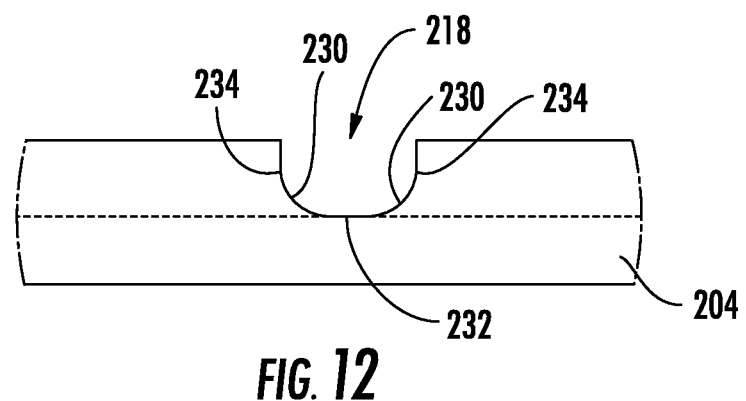
FIG. 12 is an enlarged view of the section XII of the forming groove of the forming tray shown in FIG. 11.
Figure 17:
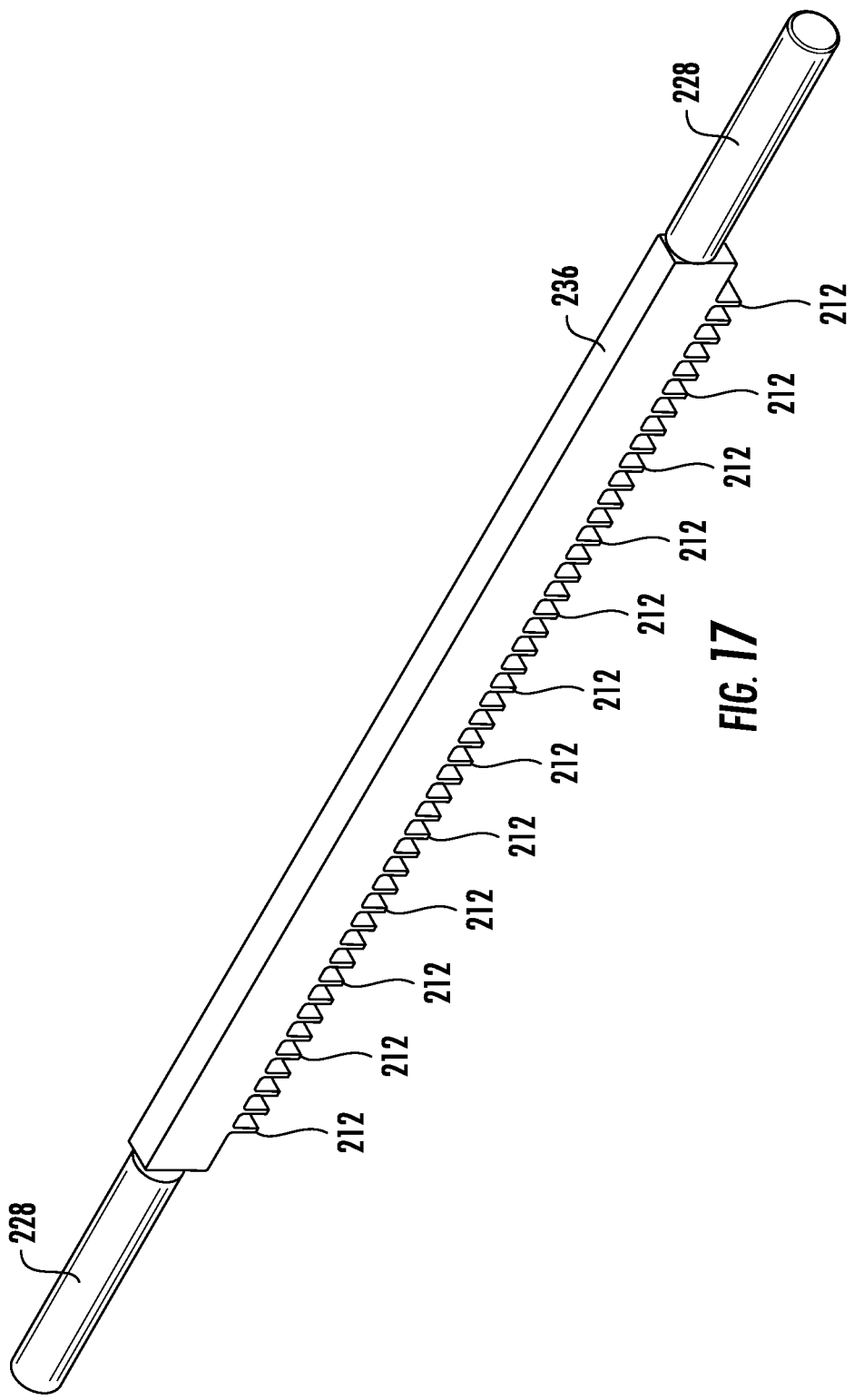
FIG. 17 is a perspective view of a spacing tool according to an aspect of the present disclosure.
Figure 18:
FIG. 18 is a top view of a spacing tool according to an aspect of the present disclosure.
Figure 19:
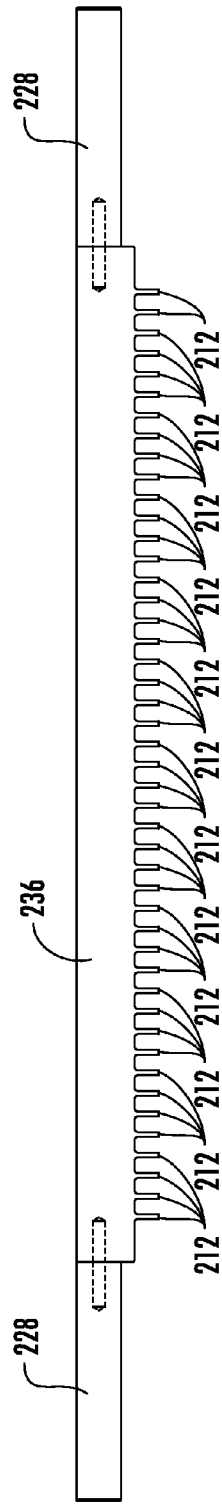
FIG. 19 is a side elevational view of a spacing tool according to an aspect of the present invention.
Figure 20:
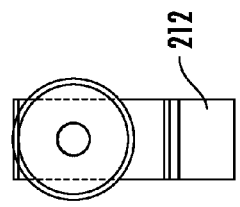
FIG. 20 is an elevated end view of a spacing tool according to an aspect of the present disclosure.

As shown in FIGS. 9-12, but especially in FIGS. 11-12, the grooves 218 of the forming tray 204 further typically have rounded side channel sections 230 running along the bottom portion of the groove proximate the bottom 232 of the groove where the sides 234 of the groove meet the bottom of the groove.

The spacing tool is shown in more detail in FIGS. 17-20. The spacing tool, as discussed above, typically incorporates two handles 228. The handles 228 of the spacing tool are typically engaged to the spacing tool bar section 236. The spacing tool bar section may have the spacing prongs 212 integrally formed therein or may have the spacing prongs engaged with the bar in some manner. Typically, the spacing prongs are integral with the bar portion as this construction typically is stronger than one where the prongs are engaged separately from the spacing tool bar section.

EXAMPLES

The following examples are presented for illustrative purposes only and are not to be interpreted as limiting the scope of the present orthodontic protection device. The examples will enable a clearer understanding of the characteristics and advantages of the invention.

Example 1

Three co-joined, approximately 2 inch segments of "ORTHOSIL™ Silicone Dental Wax" were coated with a thin film of an aqueous solution of polyvinylpyrrolidone and glycerin on what will become surfaces 104A-104E on the device. This was then placed into the "U"-shape shown in FIG. 1 and heated in an oven at 100° C. for one hour to drive most of the moisture from the hydrogel-forming layer. The heating yields a 76.9%+/−5.0% mass loss, due primarily to loss of moisture via evaporation.

Example 2

Three co-joined, approximately 2 inch segments of "ORTHOSIL™ Silicone Dental Wax" were coated with a thin film of an aqueous solution of poly (2-ethyl-2-oxazoline) and glycerin on what will become surfaces 104A-104E on the device. This was then placed into the "U"-shape shown in FIG. 1 and heated in an oven at 100° C. for one hour to drive out most of the moisture from the hydrogel-forming layer. The heating yields a 76.9%+/−5.0% mass loss, due primarily to loss of moisture via evaporation.

Example 3

Fumed-silica-filled silicone fluid was prepared by combining 13.88 g of high-viscosity silicone fluid (polydimethylsiloxane, viscosity 2,500,000 centistokes) with 1.36 g of fumed silica (surface area 400 m2/g) at a temperature of from 300° C. to 400° C. A 2 inch device as illustrated in FIG. 1 was then constructed with this material. Surfaces 104A were then coated with a thin film of an aqueous solution of polyvinylpyrrolidone and glycerin and heated in an oven at 100° C. for one hour to drive most of the moisture from the hydrogel-forming layer. The heating yields a 76.9%+/−5.0% mass loss, due primarily to loss of moisture via evaporation.

ORTHOSIL™ Silicone Dental Wax was loaded into a hand extruder and extruded through a die to prepare continuous strips of variable lengths with the shape and dimensions shown in FIG. 2. Surfaces 104A were then coated with a thin film of an aqueous solution of polyvinylpyrrolidone and glycerin and heated in an oven at 100° C. for one hour to drive most of the moisture from the hydrogel-forming layer. The heating yields a 76.9%+/−5.0% mass loss, due primarily to loss of moisture via evaporation.

Example 5

Dow Corning Q7-4550 BMG silicone HCR (Biomedical Grade High Consistency Rubber) base with nominal values of 35, 50, or 65 Shore A Durometer or mixtures thereof, was loaded into a hand extruder and extruded through a die to prepare continuous strips of variable lengths with the shape and dimensions shown in FIG. 2. Surfaces 104A-E were then coated with a thin film of an aqueous solution of polyvinylpyrrolidone and glycerin and heated in an oven at 100° C. for one hour to drive most of the moisture from the hydrogel-forming layer.

The foregoing description and Examples relate to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An orthodontic protection device comprising:
a protective layer shaped and sized to fit over a facial surface of at least one tooth of a human and any orthodontic appliances affixed to a facial surface of the at least one tooth, wherein the protective layer comprises a moldable material; and
an adhesive layer comprising a plurality of dehydrated adhesive beads including at least one hygroscopic polymeric material on a facial surface of the protective layer wherein the adhesive layer is a discontinuous coating having a plurality of droplets of adhesive on at least the facial surface of the orthodontic protection device.

2. The device of claim 1, wherein the facial surface of the device further comprises a plurality of orthodontic device receiving recesses.

3. The device of claim 2, wherein the plurality of orthodontic device receiving recesses are not created by a user and are substantially cylindrically shaped and spaced apart recesses.

4. The device of claim 1, wherein the adhesive layer further comprises a hydrophilic plasticizer that, when combined with the at least one hygroscopic polymeric material, creates a combination that has a greater plasticity than that of the hygroscopic polymeric material alone.

5. The device of claim 4, wherein the hydrophilic plasticizer is a polyol or polyol ester chosen from the group consisting of glycerin, sorbitol, xylitol, propylene glycol, polyethylene glycol having an average molecular weight of from about 200 to about 6000, and glycerin triacetate.

6. The device as recited in claim 1, wherein the device is a cuboidal shaped device sized to fit over an orthodontic brace on a single tooth and wherein the plurality of dehydrated adhesive beads are dehydrated to a moisture loss of at least about 72% wt. loss.

7. The device as recited in claim 6, wherein the facial surface of the device further comprises a cavity defined by a shape having an outer perimeter defined by an outer rim and sized to receive a single orthodontic bracket.

8. The device of claim 1, wherein the adhesive layer further comprises a plasticizer and a re-mineralization component configured to strengthen enamel of the at least one tooth.

9. The device of claim 8, wherein the re-mineralization component is chosen from the group consisting of sodium fluoride, sodium monofluorophosphate, stannous fluoride, calcium phosphate, sodium silicate, sodium phosphates, trisodium phosphate, and calcium lactate.

10. The device of claim 1, wherein the moldable material is a thixotropic semi-solid material or a mixture of thixotropic semi-solid materials that are finger pressure moldable and that once molded into a shape, retain that shape until additional pressure is applied and wherein the moldable material is finger pressure moldable without the application of heat to the moldable material.

11. The device of claim 1, wherein the moldable material has a glass transition temperature below about 37° C. and the moldable material is a polymeric material.

12. The device of claim 1, wherein the moldable material comprises a silicone polymer compounded (mixed or combined) or in a mixture with either one or both of silica or trimethylsilylated silica.

13. The device of claim 1, wherein the moldable material comprises: (1) at least one material chosen from the group consisting of polydimethylsiloxane, vinyl-functionalized polydimethylsiloxane, silanol-functionalized polydimethylsiloxane, Si—H functional silicone, and (2) one or both of silica or trimethylated silica.

14. The device of claim 1, wherein the hygroscopic polymeric material comprises at least one hygroscopic polymeric material from the group consisting of: polyvinylpyrrolidones, polyoxazolines, starches, polyacrylic acids, polyacrylates, polyvinyl alcohols, carbomers, cellulose derivatives, polysaccharides, xanthan, pectin, and guar gum, natural gums, and copolymers comprising two monomers from taken from the at least one the monomers of the hygroscopic polymeric materials listed above.

15. A method comprising the steps of:
forming a moldable material into a shape to temporarily cover an orthodontic implement in a user's mouth;
coating a surface of the moldable material with an adhesive layer by applying the adhesive layer to at least one surface of the moldable material to form an adhesive coated moldable material, wherein the adhesive layer comprises a hygroscopic polymer that form a plurality of droplets on the surface of the moldable material; and
dehydrating the adhesive layer after it is applied to the at least one surface of the moldable material and wherein the step of forming the moldable material comprises extruding the moldable material into a moldable rod and wherein the moldable material is a polymeric material having a glass transition temperature below about 37° C.

16. The method of claim 15, wherein the step of dehydrating comprises heating the adhesive coated moldable material at a temperature of from about 60° C. to about 200° C. and wherein the adhesive layer is a plurality of discontinuous beads of adhesive and the moldable material comprises a silicone polymer compounded (mixed, combined) or in a mixture with either one or both of silica or trimethylsilylated silica and wherein the method further comprises the following steps:
using a dimpling tool to create at least one cavity in a facial surface of the moldable rod prior to application of the adhesive layer; and
cutting the moldable rod into a plurality of orthodontic protection devices;
placing at least one orthodontic protection device into a container
placing a moisture barrier seal on the container to at least substantially prevent moisture migration from between an ambient environment surrounding the container and an interior of the container.

17. The method of claim 16 further comprising the steps of:
opening the container to allow access to the at least one orthodontic protection devices within the container; and
placing the facial surface of the at least one orthodontic protection devices over a brace on a tooth using a fingertip pressure applied by fingers of a human wherein the adhesive layer operates to retain the at least one orthodontic protection device in position over the brace and into engagement with the brace or the brace and the tooth; and
thereafter, using fingertip force to remove the at least one orthodontic protection device from engagement with the brace.

18. An orthodontic protection device for one tooth of a user comprising:
a finger moldable base material, shaped and sized to fit over a facial surface of the one tooth of a human and any orthodontic appliances affixed to a facial surface of the one tooth, wherein a protective layer comprises a moldable material that comprises a thixotropic semi-solid material or a mixture of thixotropic semi-solid materials; and
a plurality of dehydrated discontinuous droplets that form an adhesive layer on a facial surface of a base layer wherein the droplets comprise at least one hygroscopic polymeric material and a plasticizer.

19. The device of claim 18, wherein the finger moldable base material is finger pressure moldable and once molded into a shape, retains that shape until additional pressure is applied and wherein the moldable material is finger pressure moldable and retains the shape upon cessation of finger-pressure or other external pressure without the application of heat to the moldable material and wherein the one tooth is a permanent tooth of a human and wherein the adhesive layer is an adhesive layer comprising a series of dehydrated adhesive beads and wherein the series of dehydrated beads further comprises a re-mineralization component.

20. The device of claim 18, wherein the facial surface of the device further comprises an orthodontic device receiving recess corresponding to a single orthodontic bracket of the one tooth of the human.

* * * * *